(12) United States Patent
Steiner et al.

(10) Patent No.: US 7,780,668 B2
(45) Date of Patent: Aug. 24, 2010

(54) OSTEOCHONDRAL ALLOGRAFT CARTILAGE TRANSPLANT WORKSTATION

(75) Inventors: Anton J. Steiner, Wharton, NJ (US); James Shock, Glen Rock, NJ (US); Paul J. Mulhauser, New York, NY (US); Karl D. Kirk, III, New York, NY (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 844 days.

(21) Appl. No.: 11/712,908

(22) Filed: Mar. 2, 2007

(65) Prior Publication Data
US 2008/0255623 A1    Oct. 16, 2008

(51) Int. Cl.
*A61B 17/00* (2006.01)
*A61F 5/00* (2006.01)

(52) U.S. Cl. .............................. 606/79; 606/87; 269/87

(58) Field of Classification Search .................. 606/54, 606/79, 87; 269/41, 87, 87.3, 101, 104
See application file for complete search history.

(56) References Cited

U.S. PATENT DOCUMENTS

| | | | |
|---|---|---|---|
| 2,003,619 A * | 6/1935 | Williamson | ................ 269/87.2 |
| 4,565,192 A | 1/1986 | Shapiro | |
| 4,807,863 A | 2/1989 | Yang | |
| 5,092,572 A | 3/1992 | Litwak et al. | |
| 5,163,665 A * | 11/1992 | Klearman | ................... 269/280 |
| 5,919,196 A | 7/1999 | Bobic et al. | |
| 6,110,178 A * | 8/2000 | Zech et al. | ..................... 606/96 |
| 6,488,033 B1 | 12/2002 | Cerundulo | |
| 6,591,591 B2 | 7/2003 | Coers et al. | |
| 6,592,588 B1 | 7/2003 | Bobic et al. | |
| 6,640,666 B2 | 11/2003 | Pliley | |
| 6,852,114 B2 | 2/2005 | Cerundolo | |
| 2002/0082704 A1 * | 6/2002 | Cerundolo | ............... 623/20.35 |
| 2007/0135917 A1 * | 6/2007 | Malinin | ................... 623/16.11 |

\* cited by examiner

*Primary Examiner*—Thomas C Barrett
*Assistant Examiner*—Christine L Nelson
(74) *Attorney, Agent, or Firm*—John S. Hale; Gipple & Hale (57) ABSTRACT

A portable surgical workstation for implant formation comprising a base with a central planar section. The central planar section has a plurality of tracks and a throughgoing slot with a recessed stepped surrounding surface formed on a bottom surface of the central planar section. A vise assembly mounted to the base comprises a fixed jaw member secured to the base, a traveling jaw member moveably mounted to the base and a fixed drive housing mounted to the base. The traveling jaw member has a plurality of rail members adapted to be slidably mounted in the central planar section tracks. The fixed drive housing has a threaded longitudinal bore which receives a threaded drive shaft, one end of the drive shaft being secured in the traveling jaw member to transport the traveling jaw member.

26 Claims, 12 Drawing Sheets

OSTEOCHONDRAL ALLOGRAFT CARTILAGE TRANSPLANT WORKSTATION

RELATED APPLICATIONS

There is no related application.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present invention is generally directed toward the surgical treatment of articular chondral defects and is more specifically directed toward a surgical workstation for producing an allograft cartilage implant plug having a cartilage face and bone body.

2. Description of the Prior Art

Articular cartilage injury and degeneration present medical problems to the general population which are constantly addressed by orthopedic surgeons. Every year in the United States, over 500,000 arthroplastic or joint repair procedures are performed. These include approximately 125,000 total hip and 150,000 total knee arthroplastics and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of extracellular matrix with a sparse population of chondrocytes distributed throughout the tissue. Articular cartilage is composed of chondrocytes, type II collagen fibril meshwork, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffness to compression, resilience and durability. The hyaline cartilage provides a low friction bearing surface over the bony parts of the joint. If the cartilage lining becomes worn or damaged resulting in lesions, joint movement may be painful or severely restricted. Whereas damaged bone typically can regenerate successfully, hyaline cartilage regeneration is quite limited because of it's limited regenerative and reparative abilities.

Articular cartilage lesions generally do not heal, or heal only partially under certain biological conditions due to the lack of vascularity. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age obtained good clinical results, which most likely reflects the decreasing population of osteochondral progenitor cells with increasing age. There have also been problems with adhesion and stability of the grafts, which result in their displacement or loss from the repair site.

Transplantation of cells grown in culture provides another method of introducing a new cell population into chondral and osteochondral defects. Carticel® is a commercial process to culture a patient's own cartilage cells for use in the repair of cartilage defects in the femoral condyle marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks. Once cultivated, the cells are injected during a more open and extensive knee procedure into areas of defective cartilage where it is hoped that they will facilitate the repair of damaged tissue. An autologous periosteal flap with cambium layer is sutured around the defect to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and that biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The osteochondral plugs are harvested from a lower weight-bearing area of lesser importance in the same joint. Reports of results of osteochondral plug autografts in a small numbers of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts carry the risk of immune response or disease transmission. Musculoskeletal Transplant Foundation (MTF) has preserved fresh allografts in a media that maintains a cell viability of around 50% at 35 days for use as implants. In the current technology frozen allografts lack cell viability and have shown a decreased amount of proteoglycan content, however, they are commonly used for large defects.

A number of United States patents have been specifically directed towards the manufacture of plugs or cores which are implanted into a cartilage defect. U.S. Pat. No. 6,591,591 issued Jul. 15, 2003 describes a precut bone plug for use in allograft core transplantation surgery which has a tissue bank harvest the graft using a coring trephine with teeth having an inner diameter between 0.5 mm to 0.1 to create a bone core with a hyaline cartilage layer in approximately 7.9 mm, 9.9 mm, 11.9 mm diameters. Alternatively a donor harvester having a cutter tube with a straight cutting edge windows and depth markings with a torque handle on the proximal end may be used to obtain an allograft core as is shown in U.S. Pat. No. 5,919,196 issued Jul. 6, 1999. U.S. Pat. No. 6,592,588 issued Jul. 15, 2003 discloses instruments for cutting a bone core by cutting or punching having collared pins disposed within the harvester for removal of the harvester cores.

U.S. Pat. No. 4,565,192 issued Jan. 21, 1986 shows a multi-plate device with fixed pins and movable pins for cutting a portion of a patella during knee surgery. U.S. Pat. No. 5,092,572 discloses an allograft vise with a "V" shaped vise face and moveable vise plates. The vise is affixed to a table and can be provided with spherical vise plates having a sharp tripod support for a femur.

U.S. Pat. Nos. 6,488,033 and 6,852,114 (a divisional application of the '033 patent) issued respectively Dec. 3, 2002 and Feb. 8, 2005 are directed toward an osteochondral transplant workstation for cutting a core out of an allograft bone held in an adjustable vise with a lubricated rotary cutting bit. The core is removed from the bit, held in a specially designed set of pliers, and cut to size by a saw blade to fit into a blind bore which has been oriented and drilled into the patient's arthritic defect area. This workstation while an improvement over existing procedure is cumbersome to use and requires experience and training use.

The present invention was designed to overcome prior art procedures and provide a simple to use core preparation devise which accurately fits into the patient's bore area to form a uniform cartilage surface for the patient.

SUMMARY OF THE INVENTION

A workstation for the preparation of osteochondral allograft cartilage implants having a portable plastic base with a fixed jaw member and a moveable jaw member to hold the allograft full or hemi condyle being cut to provide replacement cores. An articulated guide assembly for a variable size positioner and cutter is mounted on the fixed jaw body and a miter for a surgical saw is formed on one side of the fixed jaw and moveable jaw.

It is an object of the invention to provide a surgical workstation for forming osteochondral allograft plugs with a cartilage layer which are of the correct size for insertion into a blind bore in a patients knee to repair a cartilage defect.

It is also an object of the invention to provide a surgical workstation allowing the creation of a cartilage repair implant which has a cartilage layer contoured to the defect site and is easily placed in a defect area by the surgeon to form a continuous cartilage surface in the defect area.

It is still another object of the invention to provide a surgical workstation for creating a cartilage implant core during surgery which has load bearing capabilities.

It is further an object of the invention to provide a surgical workstation which can be easily used by the surgeon to create correctly dimensional and contoured cartilage implants.

It is yet another object of the invention to provide a surgical workstation which can be easily cleaned and sterilized.

It is still another object of the invention to provide a workstation with a miter so that accurate core lengths for the implant can be obtained.

It is a further object of the invention to provide a surgical workstation which holds the full or hemi condyle in a fixed stable position allowing a uniform core to be cut from the hemi condyle.

These and other objects, advantages, and novel features of the present invention will become apparent when considered

DESCRIPTION OF THE INVENTION

The term "tissue" is used in the general sense herein to mean any transplantable or implantable tissue such as bone.

The terms "transplant" and "implant" are used interchangably to refer to tissue (xenogeneic or allogeneic) which may be introduced into the body of a patient to replace or supplement the structure or function of the endogenous tissue.

The terms "autologous" and "autograft" refer to tissue or cells which originate with or are derived from the recipient, whereas the terms "allogeneic" and "allograft" refer to tissue which originate with or are derived from a donor of the same species as the recipient. The terms "xenogeneic" and "xenograft" refer to tissue which originates with or are derived from a species other than that of the recipient.

The present invention is directed towards a cartilage repair implant forming workstation. The preferred embodiment and best mode of the invention is shown in FIGS. 1, 2, 3-7, and 8-10. In the inventive workstation 20, a workpiece in the form of an allograft hemi condyle 210 from which an allograft plug or core 200 with a cartilage cap 202 and a subchondral bone portion 204 is prepared for implantation into a patient.

Figure 1:
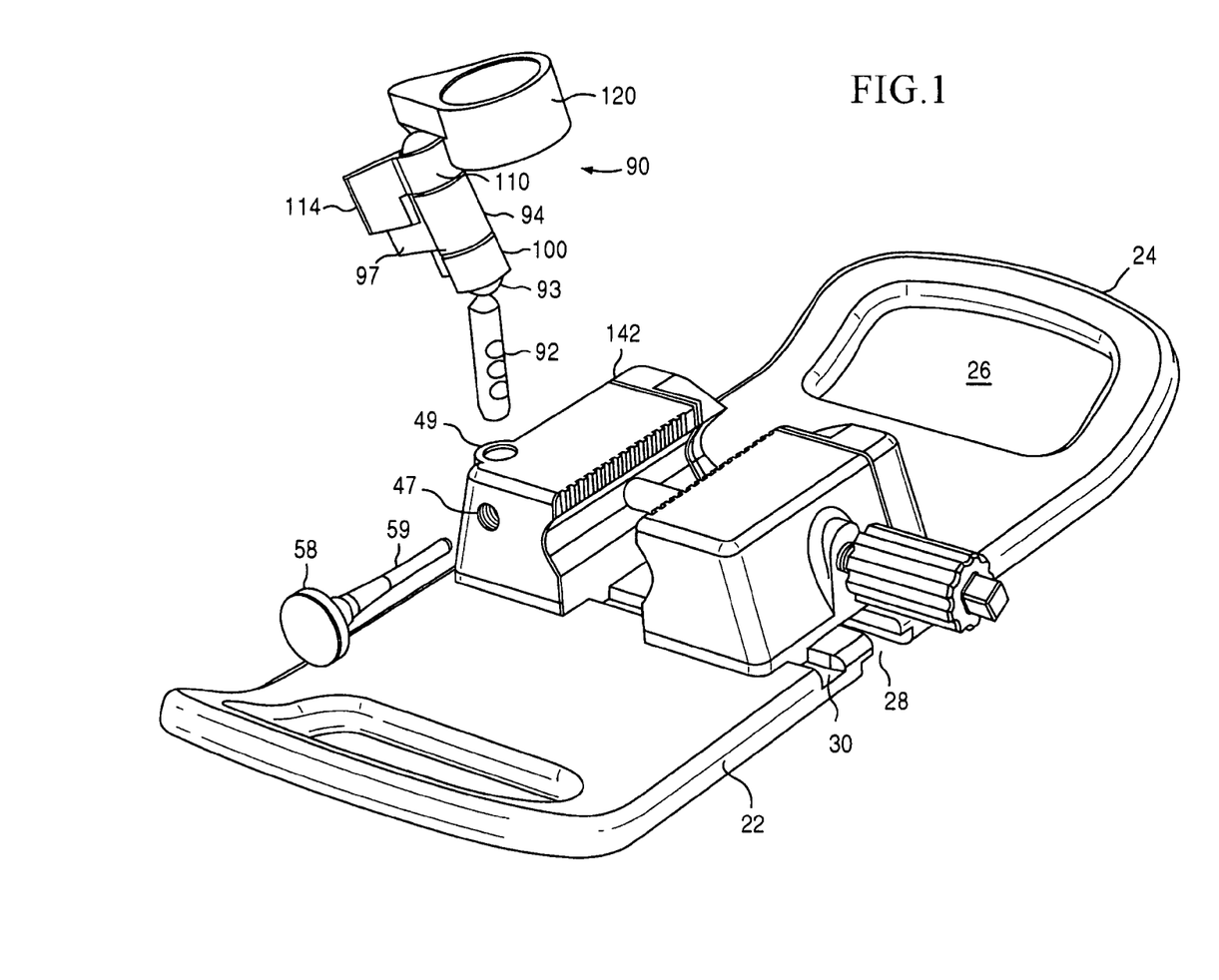
FIG. 1 is a perspective view of the osteochondral allograft cartilage implant forming workstation with an exploded cutter positioning and guide assembly.
Figure 2:
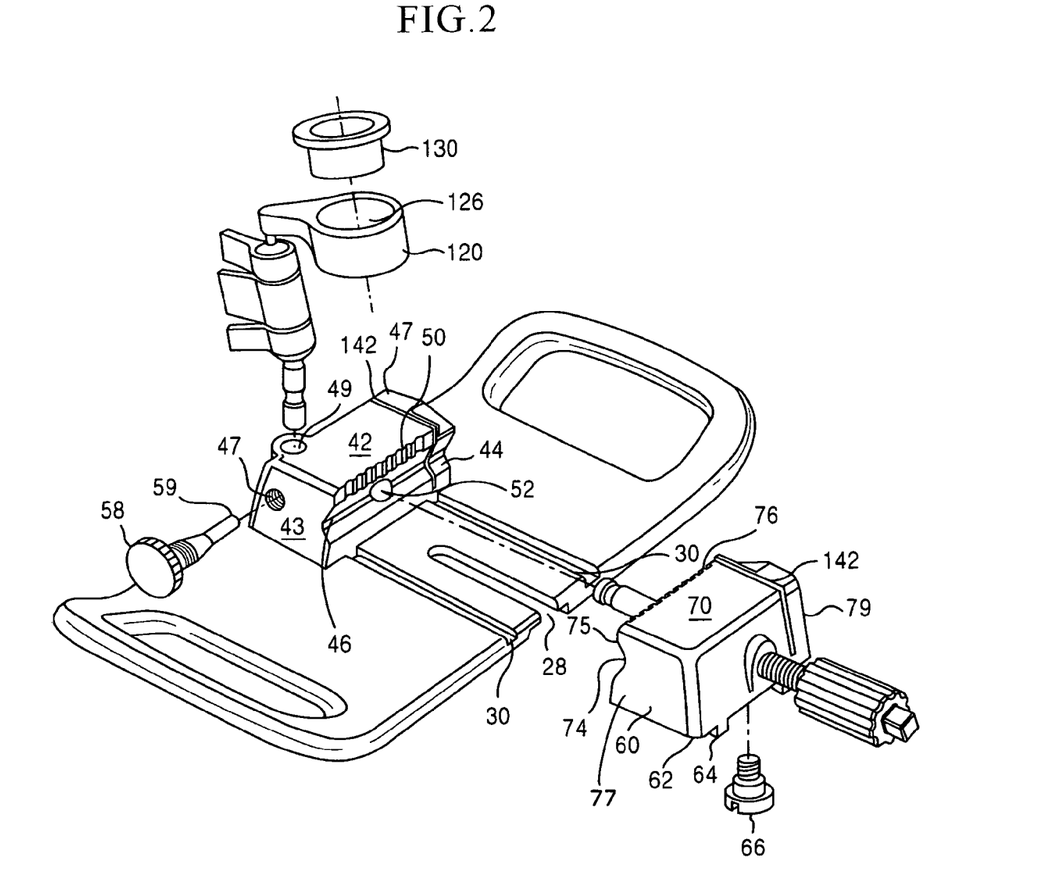
FIG. 2 is a perspective exploded view of the workstation of FIG. 1 including a bushing for the guide sleeve.
Figure 2A:
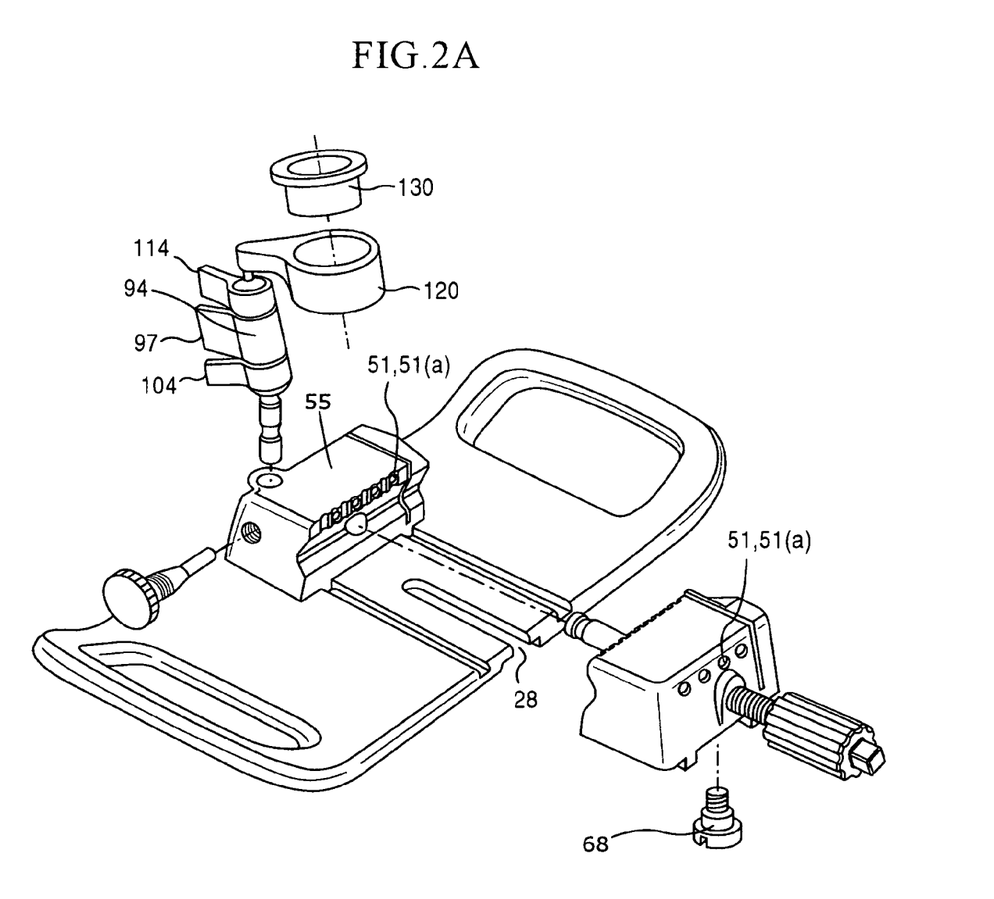
FIG. 2A is a perspective exploded view of another embodiment of the workstation of FIG. 2 showing drill guide holes for optional additional fixation of the hemi condyle including a bushing for the guide sleeve.
Figure 3:
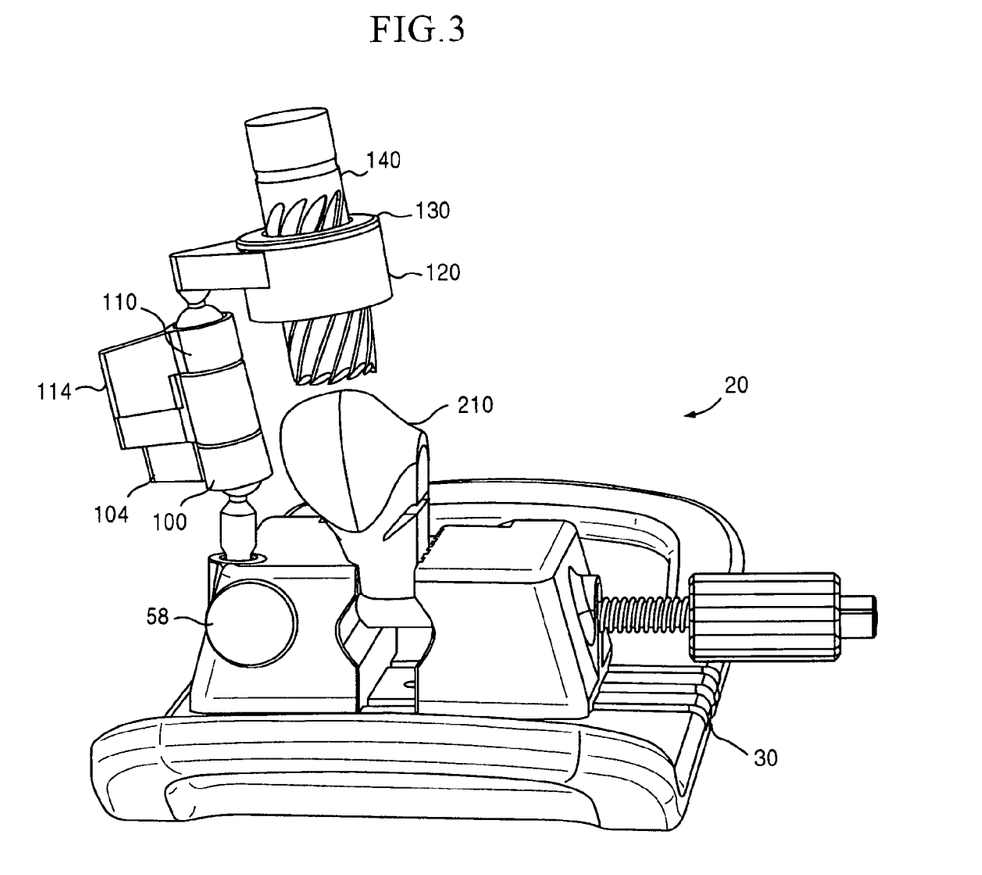
FIG. 3 is a side perspective view of the workstation shown in FIG. 1 with the cutter guide assembly in place holding the core cutter and a hemi condyle mounted in the vise jaws.
Figure 4:
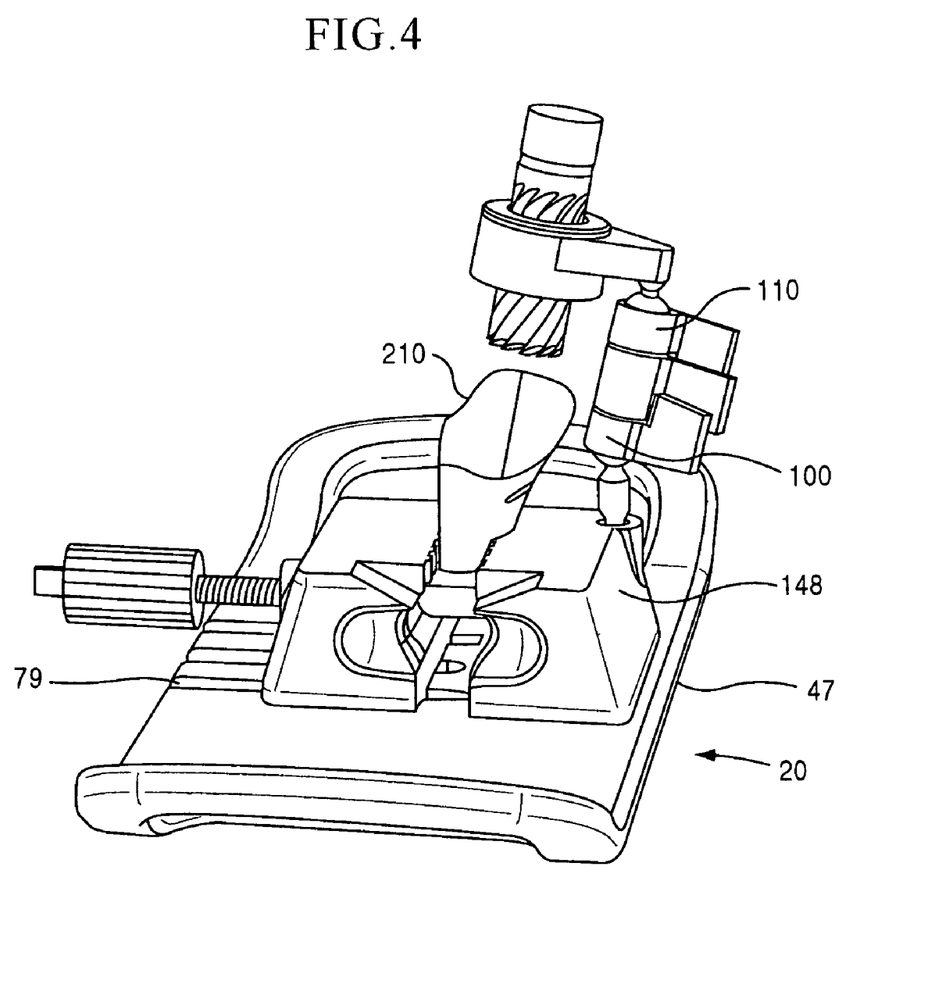
FIG. 4 is an opposite side perspective view of the workstation from that shown in FIG. 3.
Figure 6:
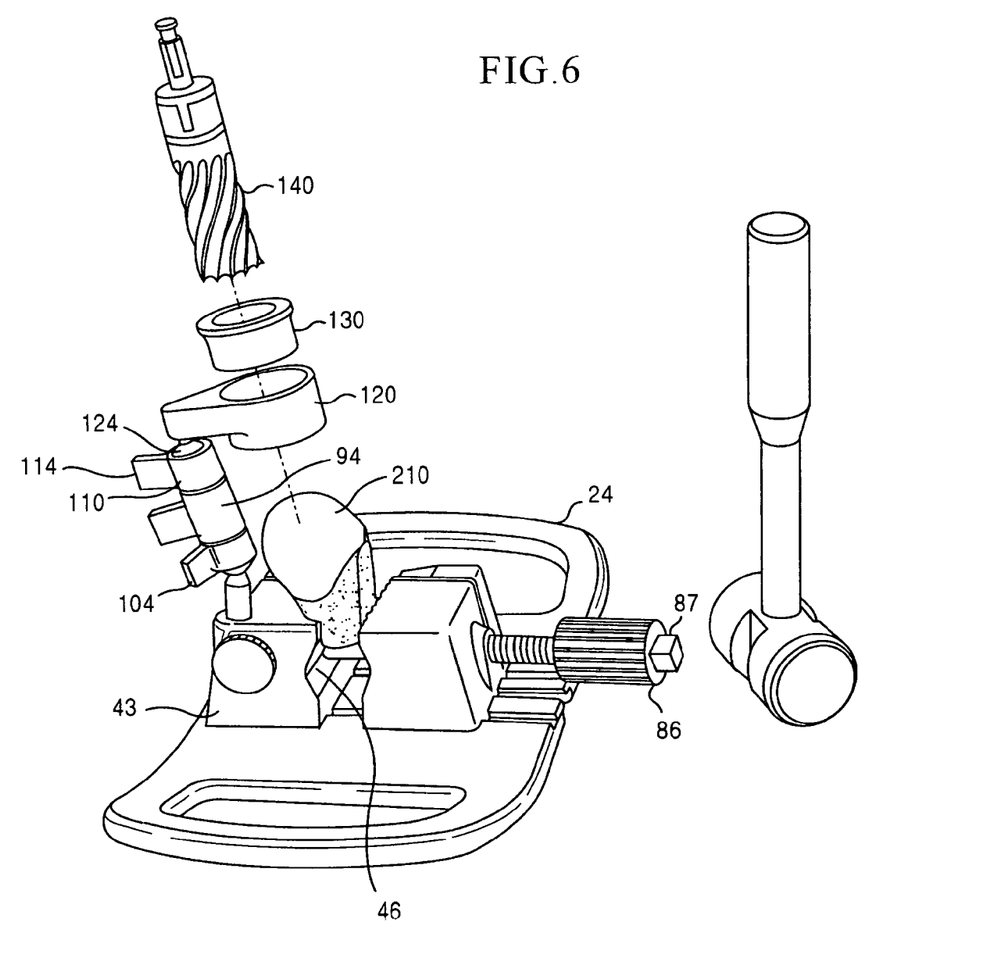
FIG. 6 is a perspective view of the osteochondral allograft cartilage implant workstation with bushing, cutter and slotted wrench tool shown in exploded position.
Figure 7:
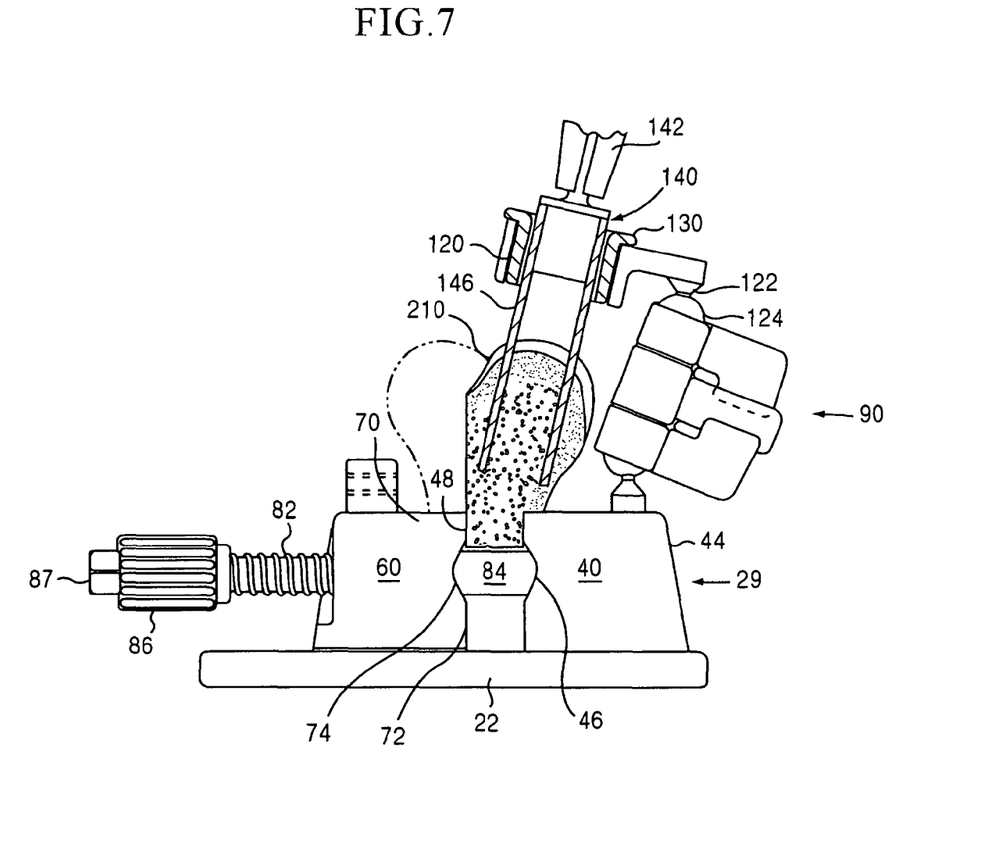
FIG. 7 is a side elevational view of the workstation shown in FIG. 6 with the cutter, cutter holder and hemi condyle shown in cross section and the cutter shown cutting the allograft cartilage implant core.
Figure 7A:
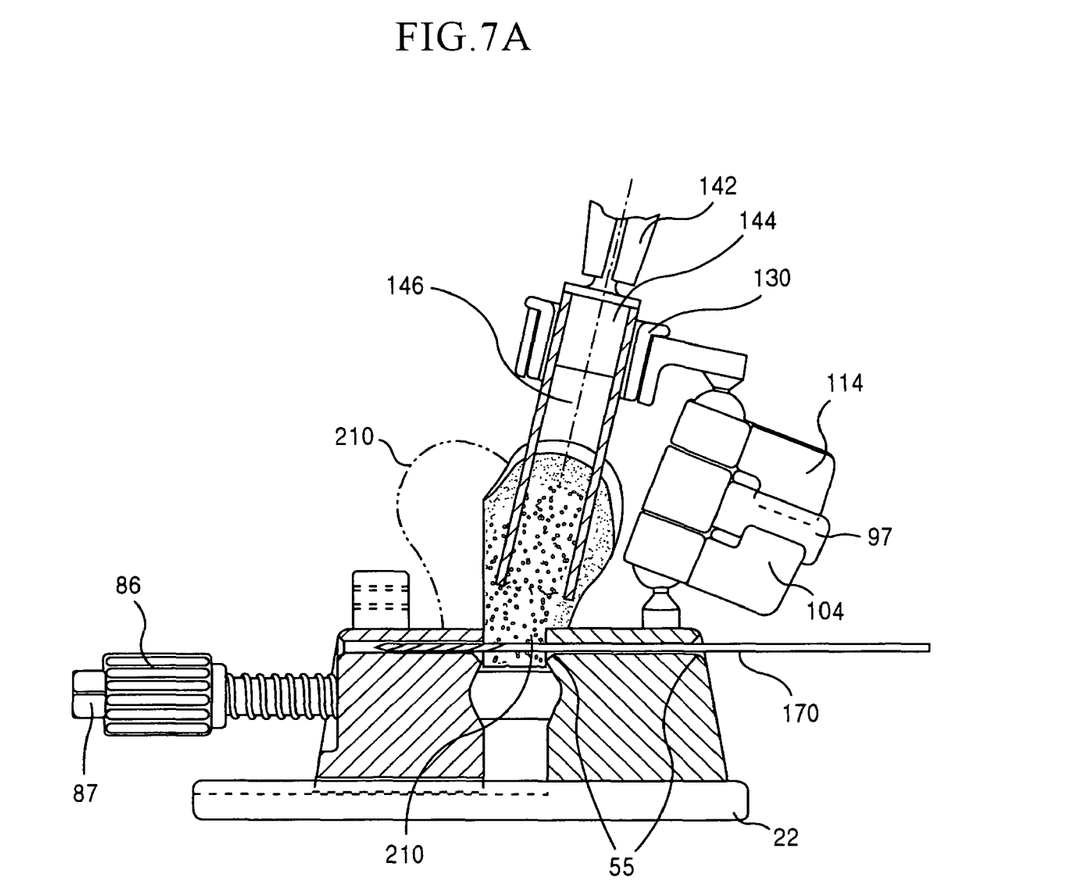
FIG. 7A is an alternate embodiment of a side elevational view of the workstation shown in FIG. 7 showing the jaws of the vise with chamfered bores used to receive wire fixation or drill bit for fixation.

The portable workstation 20 is constructed with a plastic or metal base 22 having integral upwardly angled handles 24. The angled handles 24 define grasping cutouts 26 and the base 22 defines a centrally located slot 28 which is stepped as shown in FIGS. 1, 2, 6 and 10 to receive a shoulder screw 66 which retains the traveling jaw 60 of vise 29 in the slot 28. Located on each side of slot 28 are tracks 30 which receive the rails 64 of the traveling jaw 60. The bottom surface of the base is provided with small ½ inch legs (not shown) at each corner of the base 22 which together with the grasping handles provide stability to the workstation during the cutting operations. Mounted on the top surface of base 22 is a solid fixed jaw 40 of the vise 29 having a planar top surface 42, a planar side surface 43, a rear grasping surface 44 and a front angled surface 45. The top surface 42 is planar and the associated transverse work piece grasping surface 44 (or allograft work piece engaging surface) is formed with a angular cutout 46 which receives the notch of the allograft hemi condyle 210 which has been precut prior to surgery for easy insertion into the vise 29. The top portion 48 of the grasping wall defines a plurality of vertically positioned parallel teeth 50 as best seen in FIG. 2. If desired, a plurality of parallel throughgoing drill or wire guide bores 51 as seen in FIG. 2A with chamfered hole lead ins 55 are drilled through the top portion 48 for additional fixation of the hemi condyle 210. This fixation is accomplished by wires 170 as shown in FIG. 7A or by the drill bit itself inserted through both jaws and the base of the hemi condyle 210.

Figure 10:
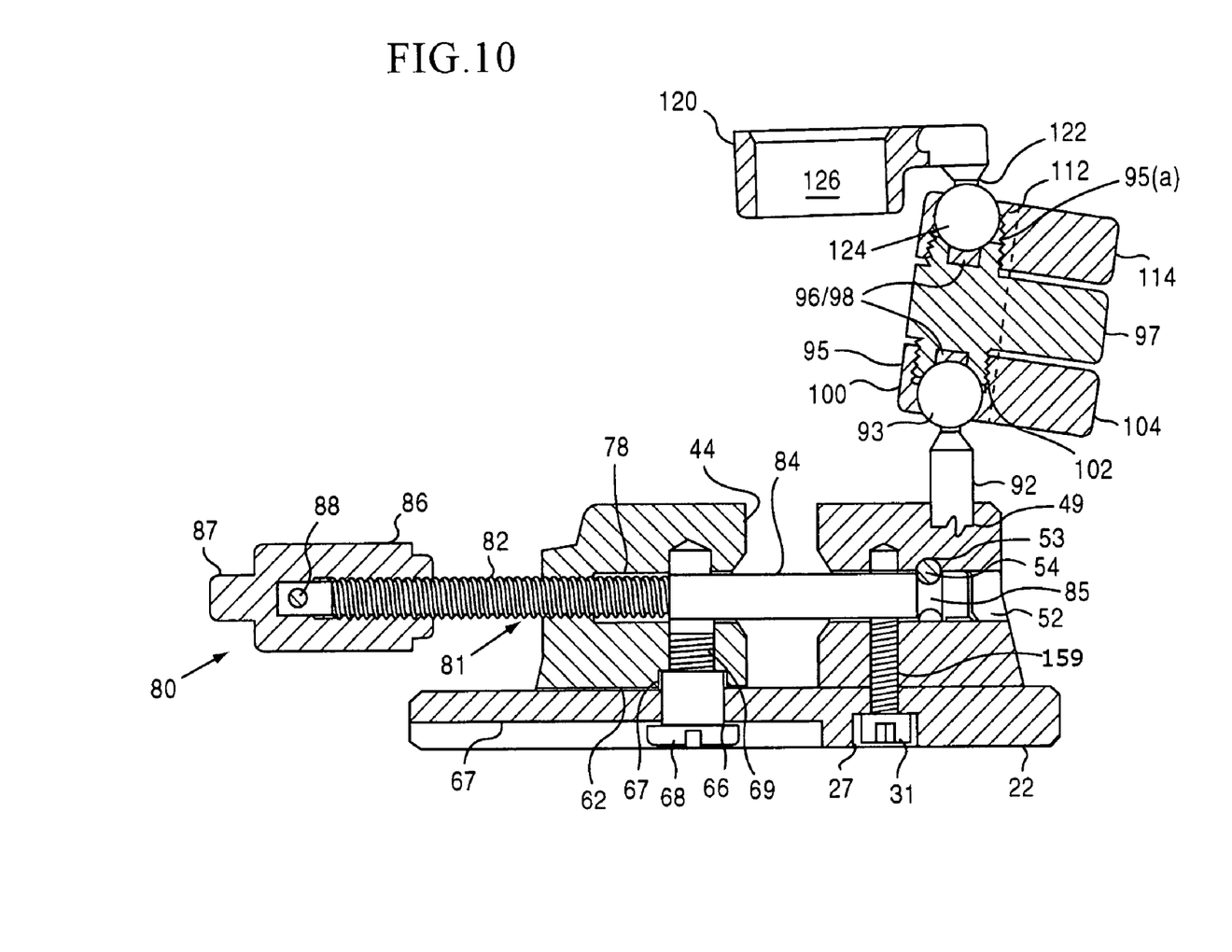
FIG. 10 is a reversed view cross section taken through the center of FIG. 4 with cutter, bushing and hemi condyle removed.

As shown in FIG. 10, a central throughgoing bore 52 is cut through the middle of the fixed jaw 40 parallel to the top surface of the base 22 to receive the shaft 81 which drives the moving jaw 60. A shaft retainer lug 54 is mounted in a groove 53 cut in the fixed jaw body adjacent the throughgoing bore 52 and extends into an arcuate groove 85 cut in the end of the shaft to keep shaft 81 in a fixed position within the fixed jaw 40. A vertical bore 49 is cut into the top surface 42 of the fixed jaw body and extends down into the fixed jaw body to receive the post 92 of the articulated arm assembly 90. A side bore 47 is cut into the side 43 of the fixed jaw body and communicates with the vertical bore 49 allowing contact of the end of shaft 59 of attachment knob 58 with the post 92 of the articulated arm assembly 90 to secure the post 92 of the articulated arm assembly at a fixed height within the fixed jaw 40. The bottom of the fixed jaw 40 is secured to the base 22 by means of recessed securement bolts 31 screwed into the bottom of the base through the recessed bores 27 in the base which are aligned with threaded blind bores 159 cut into the bottom of the fixed jaw as best seen in FIG. 10.

The moveable or traveling jaw 60 has a bottom surface 62 defining two parallel rails 64 which slide in the tracks 30 formed in the base 22. A blind bore 66 is cut into the bottom surface of the slot 28 and is axially aligned with blind stepped bore 67 cut into the bottom of the traveling jaw body. The stepped bore 67 is threaded to receive the threaded end 69 of shoulder screw 68 which retains the traveling jaw 60 in the slot 28.

Figure 9:
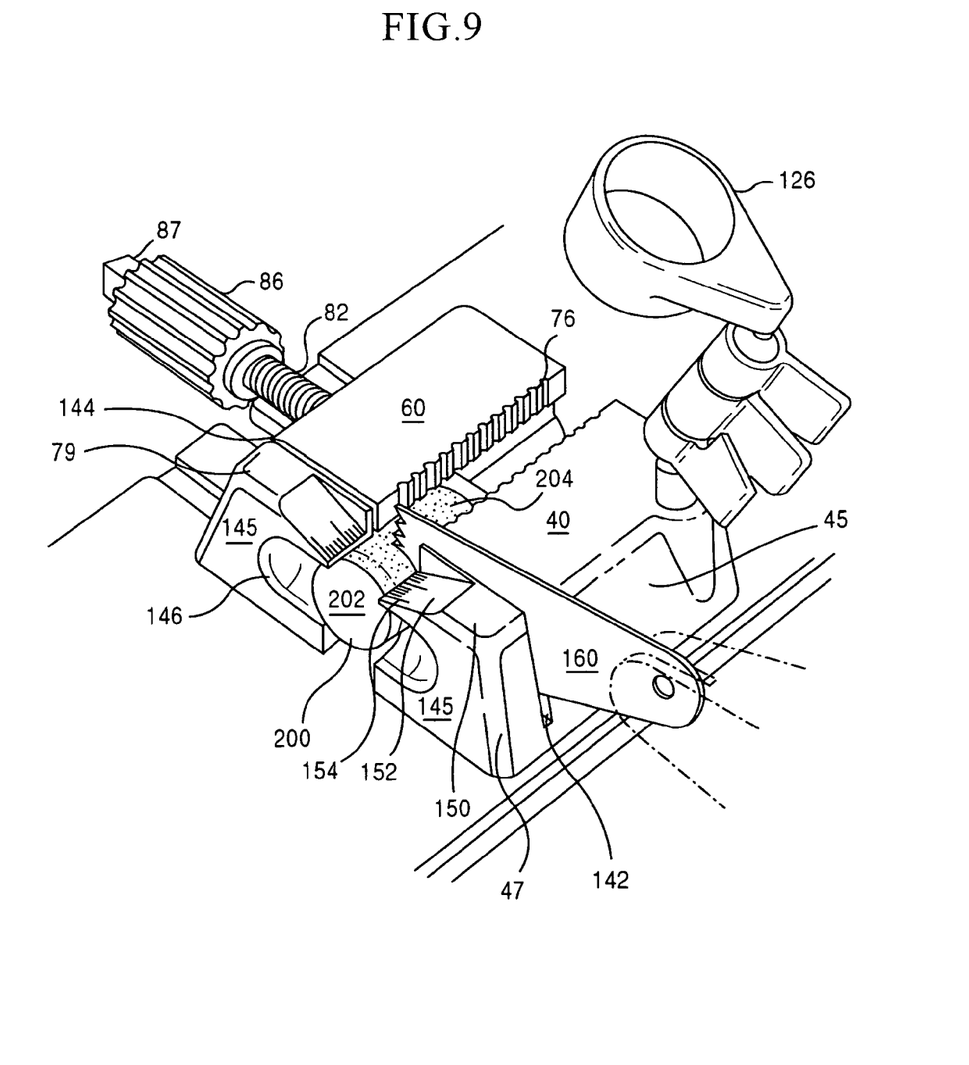
FIG. 9 is a partial enlarged perspective view of the plug length trim with the handle of the saw shown in phantom.

The surface of the top wall 70 of the moveable jaw 60 is planar and the associated transverse grasping wall 72 is formed with a angular cutout 74 which receives the notch of the allograft bone workpiece 210. The hemi condyle 210 can be mounted into the vise 29 on either axis. A planar side surface 77 forms one side of the moveable jaw 60 and a miter assembly 79 forms the opposite side of the moveable jaw. The top portion 75 of the grasping wall 72 defines a plurality of vertically positioned parallel teeth 76 as seen in FIG. 9. A plurality of parallel throughgoing drill or wire guide bores 51(a) as seen in FIG. 2A with chamfered hole lead ins 55 are drilled through the top portion 75 and are axially aligned with bore holes 51 in the fixed jaw body for additional fixation of the hemi condyle 210. This fixation is accomplished by wires 170 as shown in FIG. 7A or by the drill bit itself inserted through both jaws and the base of the hemi condyle 210.

A throughgoing bore 78 is cut through the moveable jaw body and is axially aligned with the throughgoing bore 52 of the fixed jaw body to receive threaded shaft portion 82. The thread on the shaft is an acme or convention type thread. Shaft assembly 80 comprises shaft 81 formed into threaded shaft portion 82 and a smooth surfaced shaft portion 84 with the distal smooth portion 84 of the shaft defining an arcuate groove 85 which holds shaft retainer lug 54 holding the shaft 81 fixed in place in the fixed jaw 40. The proximal portion of shaft 81 has a knob 86 mounted thereto which is held in place by a securement cross pin 88 which is best shown in FIG. 10. The proximal end of the knob 86 defines a wrench lug 87 which is adapted to receive a slotted wrench tool for tightening the vise 29.

Figure 5:
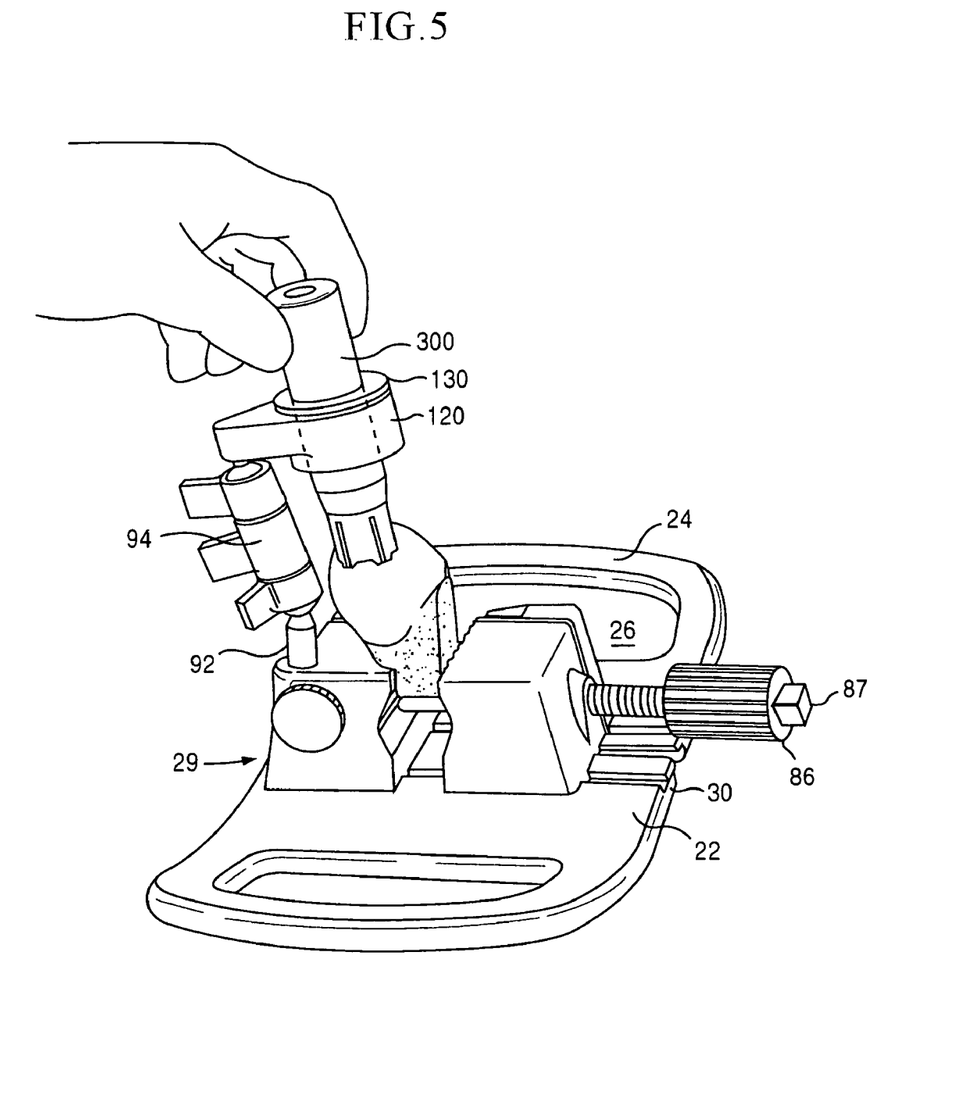
FIG. 5 is a perspective view of the allograft cartilage implant workstation using a positioner to establish donor plug position and axis.
Figure 8:
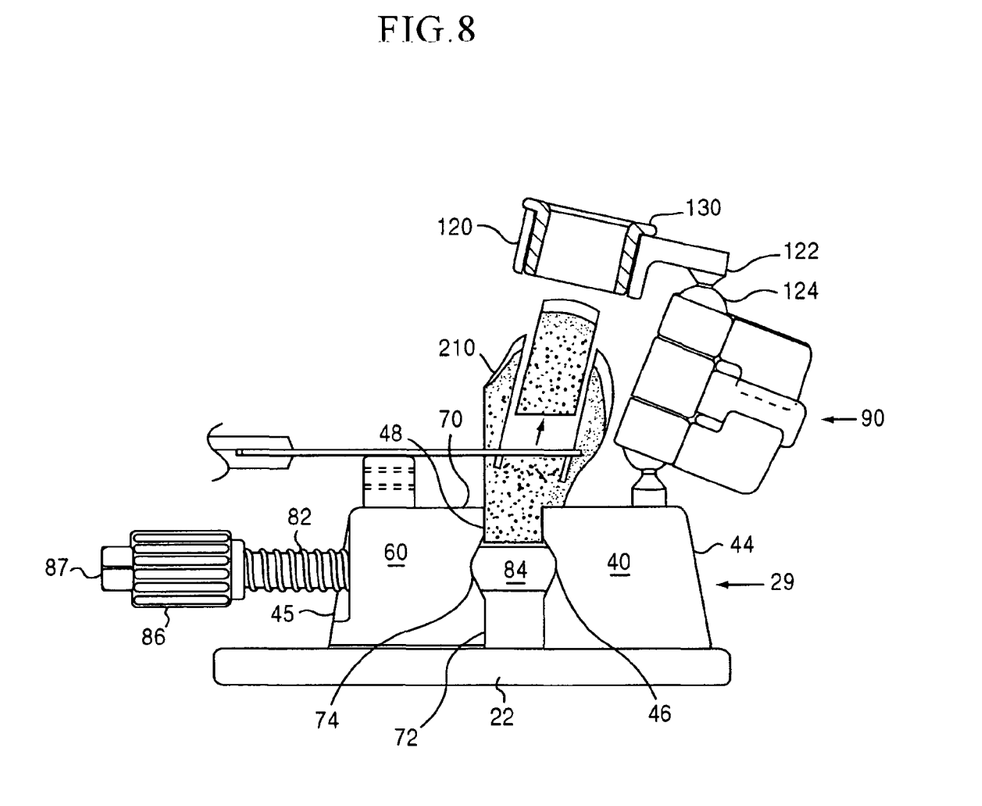
FIG. 8 is a side elevational view of the workstation shown in FIG. 7 with the cutter removed and a saw blade isolating the donor plug by cutting same to desired length.

An articulated arm assembly 90 as best seen in FIG. 10 is mounted to the fixed jaw body as previously noted. The articulated arm assembly 90 comprises a post 92 which is indexed for ease of height adjustment as shown in FIGS. 1 and 2, the distal end of the post 92 ending in an upper ball joint 93 upon which an articular arm 94 is mounted. The articular arm is positioned and locked to a designated axis as established with a sizer/positioner tool 300 as shown in FIG. 5. The articulare arm 94 is "T" shaped with tapered threaded ends 95 and 95(a), each of which defines a central recess 96 holding an acetal bearing pad 98 which respectively bears against ball joints 93 and 124. The arm 94 has an integral finger tab 97. Mounted over the lower threaded end 95 is a lower bearing lock body 100 which defines a conical threaded bore 102 sized to be threaded over the lower threaded end 95 and has an integral opposing finger tab 104 for locking end 95 in place against ball joint 93. Mounted over the upper threaded end 95a is an upper bearing lock body 110 which defines a conical threaded bore 112, the lock body 110 having an integral opposing finger tab 114 for locking end 95(a) in place against ball joint 124. The upper bearing lock 110 holds a positional collar 120 which has an extending arm 122 with a ball joint 124 secured to the distal end which is held in a fixed position by the upper bearing lock body 110. The collar 120 defines a central throughgoing bore 126 which can hold interchangeable bushings 130 as shown in FIG. 6-8 ranging in size from 15, 18, 20, 22, 25, 30 and 35 mm in diameter. The bushings in turn are adapted to hold core cutter blades 144 ranging from 15, 18, 20, 22, 25, 30 and 35 mm in diameter.

A plug or core cutting assembly 140 comprising an arbor 142, chuck 144 and cylindrical cutting blade 146 are shown in FIGS. 7, 7A. The core trimmer is formed in the fixed jaw 40 and the moveable jaw 60 as best seen in FIG. 9. Each jaw side portion 47, 79 defines an aligned miter slot 142, 144 which establishes a perpendicular cut to match the bottom of the recipient counterbore with the exterior side 145 of miter side portions 47, 79 defining finger clearance reliefs 146. The miter slot is of sufficient width to receive a standard type surgical saw blade 160. The top surface 148 of each of the miter sections has a flat planar section 150 and a downward angled flat surface 152 with the ends being provided with a scale 154 set to the allograft plug length.

In operation, the lesion or defect is removed by cutting a counterbore in the patient of a predetermined diameter and depth in the defect area with a cannulated boring bit. An allograft hemi condyle is placed between the jaws of the vise to hold the condyle in the desired position. A donor cutting guide is placed over the allograft condyle in the same position and orientation as the original cartilage removed from the defect area and then a coring bit and arbor is used to obtain an allograft plug of the same diameter as the diameter of the core cut into the defect area of the patient as seen in FIG. 1. The core is then removed from the allograft condyle by sawing the condyle transversely with a surgical saw as seen in FIG. 8 to make the allograft plug an independent entity. The plug is then trimmed to length by the surgical saw in the miter cutting area as shown in FIG. 9 or when held by forceps.

The plug 200 which has been cut to the desired length is placed in the bore which has been cut in the lesion area of the bone of the patient with the upper surface of the cartilage cap 202 being slightly proud or substantially flush with the surface of the original cartilage remaining in the area. The length of the osteochondral plug 200 can be the same as the depth of the bore or less than the depth of the bore If the plug 200 is the same length, the base of the plug implant is supported and the articular cartilage cap 202 is level with the articular cartilage of the patients bone surface. If the plug is of a lesser length, the base of the plug implant is not supported but support is provided by the wall of the bore or respective cut out area as the plug is interference fit within the bore or cut out area with the cap being slightly proud or flush with the articular cartilage depending on the surgeon's preference. With such load bearing support the graft surface is not damaged by weight or bearing loads which can cause micromotion interfering with the graft interface producing fibrous tissue interfaces and subchondral cysts.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. A surgical workstation for implant formation comprising a base, a vise assembly mounted to said base, said vise assembly comprising a fixed jaw member and a moveable jaw member, drive means connected to said moveable jaw member for transporting said moveable jaw toward and away from said fixed jaw, articulated guide means mounted directly to said fixed jaw member, said articulated guide means including a sleeve member and a plurality of moveable interconnected members and a miter cutting assembly positioned adjacent said vise assembly, said miter cutting assembly defining a slot of a width to receive a surgical saw.

2. A surgical workstation as claimed in claim 1 wherein said base comprises a central planar section and integral handles extending from said central planar section.

3. A surgical workstation as claimed in claim 2 wherein said integral handles are angularly positioned with respect to said central planar section and define cutouts for grasping.

4. A surgical workstation as claimed in claim 1 wherein said fixed jaw member defines a longitudinal bore which receives a drive shaft, said drive shaft being secured in said fixed jaw to preclude axial movement while retaining rotational movement.

5. A surgical workstation as claimed in claim 1 wherein said fixed jaw member and said moveable jaw member each have a grasping surface which defines a recess to hold a work piece.

6. A surgical workstation as claimed in claim 5 wherein said recess is angular in shape.

7. A surgical workstation as claimed in claim 5 wherein each grasping surface is provided with a plurality of teeth.

8. A surgical workstation as claimed in claim 1 wherein said miter cutting assembly comprises a first cutting block mounted to said fixed jaw and a second cutting block mounted to said moveable jaw, each cutting block defining a slot having a width sufficient to receive a surgical saw.

9. A surgical workstation as claimed in claim 8 wherein each of said first and second cutting blocks has an upper surface with a top planar portion and a downward angled planar portion.

10. A surgical workstation as claimed in claim 9 wherein said downwardly planar angled portion is provided with measuring indicia.

11. A surgical workstation as claimed in claim 1 wherein said drive means comprises a shaft with a smooth outer surface portion and a threaded portion and a handle secured to said threaded portion.

12. A surgical workstation as claimed in claim 11 wherein said smooth shaft portion has an arcuate groove around its circumference adapted to receive stop means mounted in said fixed jaw member.

13. A surgical workstation as claimed in claim 12 wherein said stop means is a lug.

14. A surgical workstation as claimed in claim 1 wherein said articulated guide means comprises a plurality of threaded interconnected members with ball joint means at each end, the ball joint means located furtherest from said fixed jaw member having a guide sleeve mounted thereto.

15. A surgical workstation as claimed in claim 14 including bushing means mounted in said guide sleeve.

16. A surgical workstation as claimed in claim 14 wherein one ball joint means comprises a post with height indicators and a ball joint secured to a distal end of said post.

17. A surgical workstation as claimed in claim 1 wherein said fixed jaw and said moveable jaw are each provided with a plurality of parallel throughgoing bores which are axially aligned with the bores of the opposing jaw.

18. A portable surgical workstation for forming a cartilage implant comprising a base having a central planar section and handles extending therefrom, a vise assembly mounted to said base, said vise assembly comprising a fixed jaw member and a moveable jaw member, drive means mounted in said fixed jaw member and threadably connected to said moveable jaw member for transporting said moveable jaw member toward and away from said fixed jaw member, each jaw member defining a workpiece grasping surface, an articulated guide means mounted directly to said fixed jaw member, said articulated guide means comprising a post with a ball joint, a plurality of moveable interconnected members mounted on said ball joint and a sleeve assembly mounted to at least one of said interconnected members and a miter cutting assembly defining a slot of a width to receive a surgical saw mounted to at least one of said jaw members.

19. A portable surgical workstation as claimed in claim 18 wherein said sleeve assembly comprises a sleeve member, an arm extending from said sleeve member and a ball joint mounted on said extended arm.

20. A portable surgical workstation as claimed in claim 18 wherein said drive means comprises a shaft having a threaded portion and a smooth surface portion and a handle mounted on said threaded portion.

21. A portable surgical workstation as claimed in claim 18 wherein said base defines a stepped slot and said moveable jaw member has guide means mounted thereto which extend into said stepped slot to guide said moveable jaw member in a linear direction.

22. A portable surgical workstation as claimed in claim 18 wherein said base defines at least one groove and said moveable jaw has at least one rail extending therefrom mounted in said at least one groove.

23. A portable surgical workstation as claimed in claim 18 wherein said workpiece grasping surface defines an angular recess.

24. A surgical workstation for implant formation comprising a base, a vise assembly mounted to said base, said vise assembly comprising a fixed jaw member and a moveable jaw member, each jaw member defining a workpiece grasping surface having a plurality of teeth, drive means comprising a shaft having a threaded portion and a smooth surface portion and a handle mounted on said threaded portion, said smooth surface portion being rotatably moveable, said fixed jaw member and said threaded portion being connected to said moveable jaw member for transporting said moveable jaw toward and away from said fixed jaw, articulated guide means mounted directly to said fixed jaw member, said articulated guide means including a sleeve member and a plurality of moveable interconnected threaded members and a miter cutting assembly mounted to at least said moveable jaw member defining a slot of a width to receive a surgical saw.

25. A surgical workstation as claimed in claim 24 wherein said fixed jaw member and said moveable jaw member are each provided with a plurality of parallel throughgoing bores which are axially aligned with the bores of the opposing jaw member.

26. A surgical workstation and associated kit of accessory devices for implant formation comprising a base, a vise assembly mounted to said base, said vise assembly comprising a fixed jaw member and a moveable jaw member, drive means connected to said moveable jaw member for transporting said moveable jaw toward and away from said fixed jaw, articulated guide means mounted directly to said fixed jaw member, said articulated guide means including a sleeve member and a plurality of moveable interconnected members and a miter cutting assembly defining a slot of a width to receive a surgical saw on said base, said kit devices comprising plurality of different inner diameter bushings adapted to fit in said sleeve member and different diameter cylindrical core cutter assemblies sized to fit in a respective diameter sized bushing.

* * * * *